United States Patent [19]
Black et al.

[11] Patent Number: 5,163,936
[45] Date of Patent: Nov. 17, 1992

[54] ENDOSCOPIC MIRROR LASER BEAM DELIVERY SYSTEM AND METHOD FOR CONTROLLING ALIGNMENT

[75] Inventors: Michael Black, Foster City; Vladimir Kupershmidt, Fremont, both of Calif.

[73] Assignee: Reliant Laser Corp., Foster City, Calif.

[21] Appl. No.: 643,279

[22] Filed: Jan. 22, 1991

[51] Int. Cl.$^5$ .............................. A61B 17/36
[52] U.S. Cl. .................... 606/18; 359/859; 606/2; 128/4
[58] Field of Search .......... 606/2, 3, 10, 11, 12, 606/13, 14, 18; 128/4, 6; 359/726, 727, 729, 731, 859, 625-627, 618, 657, 658, 660, 661

[56] References Cited

U.S. PATENT DOCUMENTS

| | | | |
|---|---|---|---|
| 2,520,634 | 8/1950 | Grey | 359/859 |
| 3,865,114 | 2/1975 | Sharon | 606/18 |
| 4,315,130 | 2/1982 | Inagaki et al. | 219/121 LA X |
| 4,573,467 | 3/1986 | Rich et al. | 606/18 |
| 4,653,880 | 3/1987 | Sting | 359/859 |
| 4,863,253 | 9/1989 | Shafer et al. | 359/859 |
| 5,074,859 | 12/1991 | Koziol | 606/18 |

FOREIGN PATENT DOCUMENTS 936932  6/1982  U.S.S.R. .................... 606/18

Primary Examiner—Peter A. Aschenbrenner
Attorney, Agent, or Firm—David Pressman

[57] ABSTRACT

An endoscopic mirror laser beam delivery system, e.g., for laser surgery, comprises a beam splitting module (22) for optical connection to a laser beam source (14) which supplies a low-power aiming beam (12) and a high-power surgical beam (10) to the splitting module (22); a two-mirror focusing unit (24) optically connected to the splitting unit (22); and an endoscopic tube (20) for guiding the beams focused by the focusing unit (24) to a target point (P). The system also comprises a method for checking alignment of the optical system by observing the positions of two visible beam spots. In case of misalignment, these two spots do not coincide in a single point, thereby indicating misalignment which can be then corrected. The system and the method eliminate central obscuration and misalignment of the laser beams on an operation site, thereby enabling a surgeon to be able to be confident that the surgeon beam will impinge precisely upon the spot delineated by the aiming beam.

5 Claims, 3 Drawing Sheets

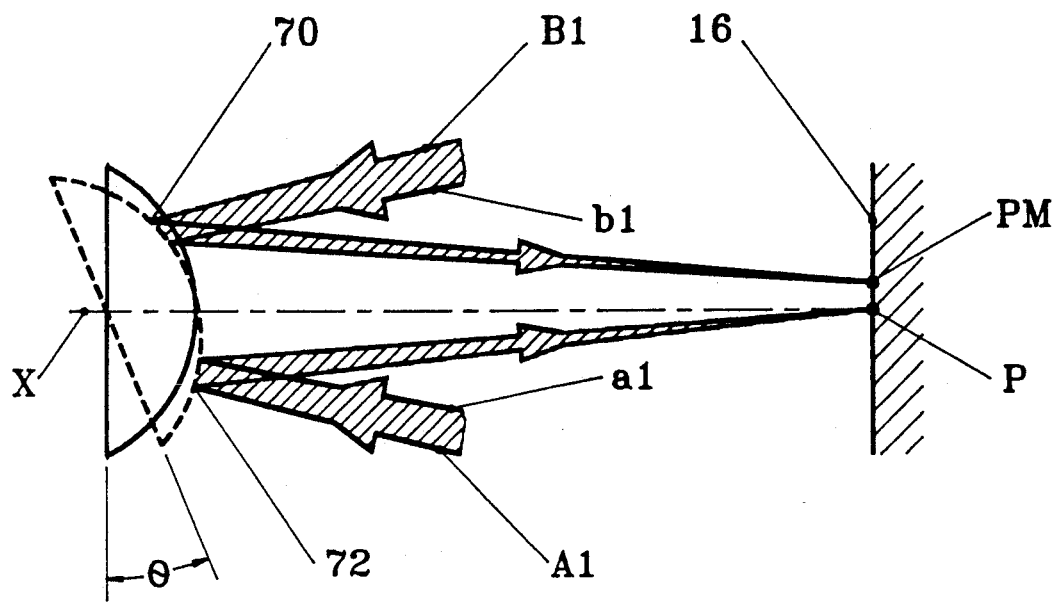
Fig.4
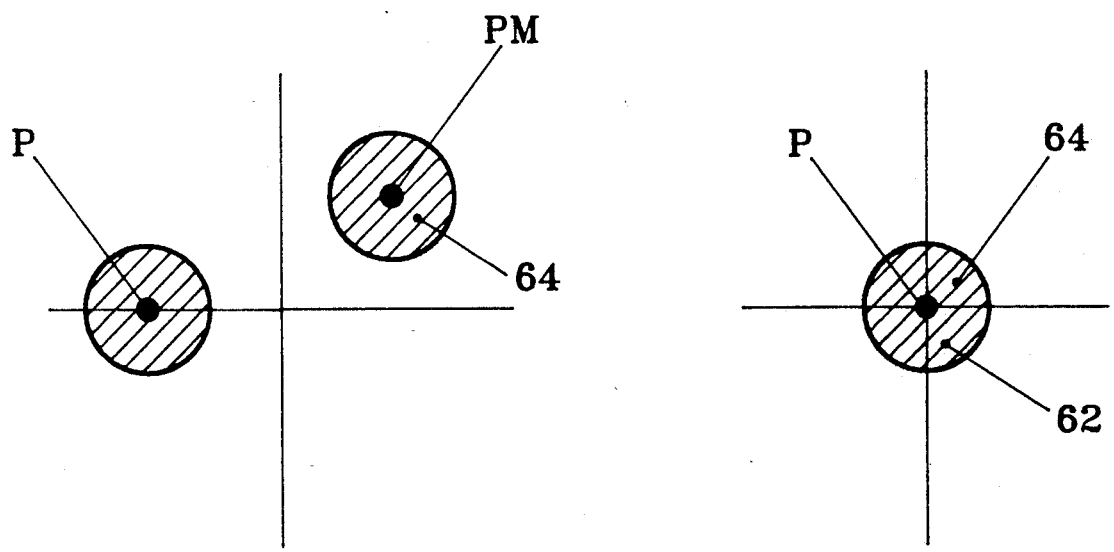
Fig.5                    Fig.3

ENDOSCOPIC MIRROR LASER BEAM DELIVERY SYSTEM AND METHOD FOR CONTROLLING ALIGNMENT

BACKGROUND

1. Field of the Invention

The present invention relates to the field of laser optics, particularly to a mirror laser beam delivery systems used, e.g., in laser surgery, especially with a surgical endoscope. The invention also relates to a method for controlling alignment of such systems.

2. Description of Prior Art

At the present time laser techniques find increasing medical applications, in particular in laser surgery. For carrying out an operation with the use of a laser, a laser beam should be delivered to the operation site, but such sites usually are located remotely from the source of laser energy and are very often poorly accessible.

Optical systems used for delivering laser energy to the operation or treatment site are known as laser beam delivery systems. Usually such systems are built into an endoscope, which is an instrument used for visually examining the interior of body cavities.

Typically, a laser apparatus for surgical applications employing an endoscope consists of two laser beam systems which operate on different wavelengths. One laser beam system is used to generate a visible, low-power beam which indicates the target area. The second laser beam system, which is aligned with the first one, is used to provide a high-power beam which operates on an invisible wavelength. The surgeon using the apparatus guides the low-power visible beam via the endoscope to the selected site in the operation area by observing its position and then activates the power or surgical beam so that it will impinge (via the endoscope) onto such site. The visible beam has lower energy than the level required for treating an object, while the power beam has a level of energy capable of burning or ablating tissue and thus performing the operation. One typical system of this type is described in U.S. Pat. No. 4,917,083 to J. Harrington and M. Clancy, 1990.

At the present time all laser beam focusing systems (which operate through an endoscope or without an endoscope) use optical lenses as their main focusing elements. Such a focusing system, which is known as a telescope, usually consists of a tubular housing, which contains a number of lenses arranged on the general optical path and intended for focusing both laser beams on the operation area. One such system is sold under the mark Micromanipulator Model 5000 by Coherent, Inc., Palo Alto, Calif. In operation, the user, depending on the type of the procedure, must select a proper distance between the target and the outlet end of the focusing unit to insure either focusing or defocusing conditions, depending on the type of the operation.

It is known, however, that all lens type systems have refraction indexes dependent upon the wavelength of the laser beam used in the system. This causes problems which in practice cannot be solved completely. More specifically, if the power or invisible beam is in the far infrared wavelength range, i.e., 10.6 microns, and the guide, or visible beam has a wavelength of 0.632 micron, both beams will be refracted differently by the optical system. This is known as chromatic aberration.

Thus, any laser beam delivery system based on the use of optical lenses is unequivocally dedicated only to one predetermined power beam laser source wavelength. This means that each time the user wants to change the laser wavelength, for example, for changing type of a surgical procedure, such user has to replace the laser beam delivery system. All of the above will not allow the surgeon to switch from one type of the laser source to another without changing the original setup. Thus, the surgeon must purchase an additional optical delivery system (at substantial cost) for a different specific wavelength.

Aberration is a failure of a lens system to produce point-to-point correspondence between an object and its image. Chromatic aberration occurs in optical systems which act upon light of different wavelengths. In other words, two coaxial laser beams of different wavelengths incident on the same point are refracted by the system to different degrees and thus cannot be focused exactly upon the same target point by a single system.

It is also well known from optics that lights of different wavelengths, and therefore laser beams of different wavelengths, are absorbed differently; this can lead to substantial energy losses and inaccuracy. This means that existing apparatus of the optical type are not sufficiently accurate and therefore, unreliable and unsuitable for critical surgical procedures. A surgeon thus cannot be absolutely confident that both beams will be coincident on the same point and with the same spot size.

The problems of laser optical systems described above have been partially solved by applicants with the use of a method and apparatus for transmitting and steering laser beams described in their earlier U.S. patent application Ser. No. 07/576,790, filed Sept. 4, 1990. The method and apparatus disclosed in the above application are based upon the use of a two-mirror delivery system for the delivery of laser beams to the operation site. Since a mirror system does not produce chromatic aberration, the problem of inconsistency between laser sources (with fixed wavelengths) and laser beam delivery system was solved.

However, the two-mirror laser beam delivery system did not solve a problem of misalignment which may occur when the two coaxial beams were presumably focused at one point. This occurred when the visible beam was deflected from the desired position, e.g., due to misalignment, the surgeon will see the absolute position of the visible beam, but not its deflection relative to the optical axis. This is because the optical axis is an imaginary axis and cannot be physically seen. Such conditions prevented the surgeon from being confident that both beams were precisely aligned.

In addition, two-mirror systems of the type described above introduce a phenomenon which is known as central obscuration, i.e., blocking of a portion of a light beam by a smaller mirror which interferes with the path of the laser beam being delivered.

Everything described above relates to laser beam delivery systems in general. However, in addition to the problems concerning laser beam delivery systems, their incorporation into an endoscope also results in specific problems. As is known, current endoscopic laser surgery is performed with one of two types of endoscope attachments, i.e., a waveguide device with reflecting internal surfaces, and a focusing endoscope that passes the laser beam intact through an internal tube.

Since waveguide devices are characterized by diversion of the beam at the output end of the endoscope, they are applicable only when the output end of the endoscope is in direct contact with the tissue to be treated.

As far as the focusing endoscope is concerned, it allows a certain short distance between the end of the endoscope and the operation area. However, such an endoscopic tube cannot pass the entire laser beam which enters the tube without clipping a substantial portion of its energy. Otherwise it would be necessary to employ an extremely expensive and complicated optical system which would make the endoscopic system economically unjustifiable.

Furthermore, conventional systems described above have a "rigid", i.e., non-adjustable structure which does not allow elimination of slight misalignment which may occur in the system.

For the reasons described above, conventional endoscopic laser beam delivery systems have significant problems, such as large spot sizes, poor alignment of the aiming and surgical laser beams, and large transmission losses.

OBJECTS AND ADVANTAGES OF THE INVENTION

It is therefore an object of the invention to eliminate the above disadvantages and to provide an improved endoscopic laser beam delivery system which ensures visual control of alignment and focusing of two coaxial beams. Another object is to provide the above system which eliminates central obscuration of laser beams delivered by the system to an operation site. A further object is to provide an endoscopic laser beam delivery system which ensures small spot sizes, improved alignment of beams, reduced transmission losses, and the ability to operate in areas remote from the outlet end of the endoscopic tube. A still further object is to provide a new and reliable method for visually controlling alignment and focusing of power and aiming beams to a target point. Other features and advantages of the invention will become apparent after consideration of the ensuing description with accompanying drawings.

BRIEF DESCRIPTION OF DRAWING

FIG. 3 is a view of a vision site showing an aiming beam spot aligned with a surgical beam spot.

FIG. 4 is schematic optical diagram illustrating deviation of the beams in a misaligned system.

FIG. 5 show the positions of the spots when the optical laser beam delivery system is misaligned.

REFERENCE NUMERALS USED IN DRAWINGS AND DESCRIPTION

Figure 1:
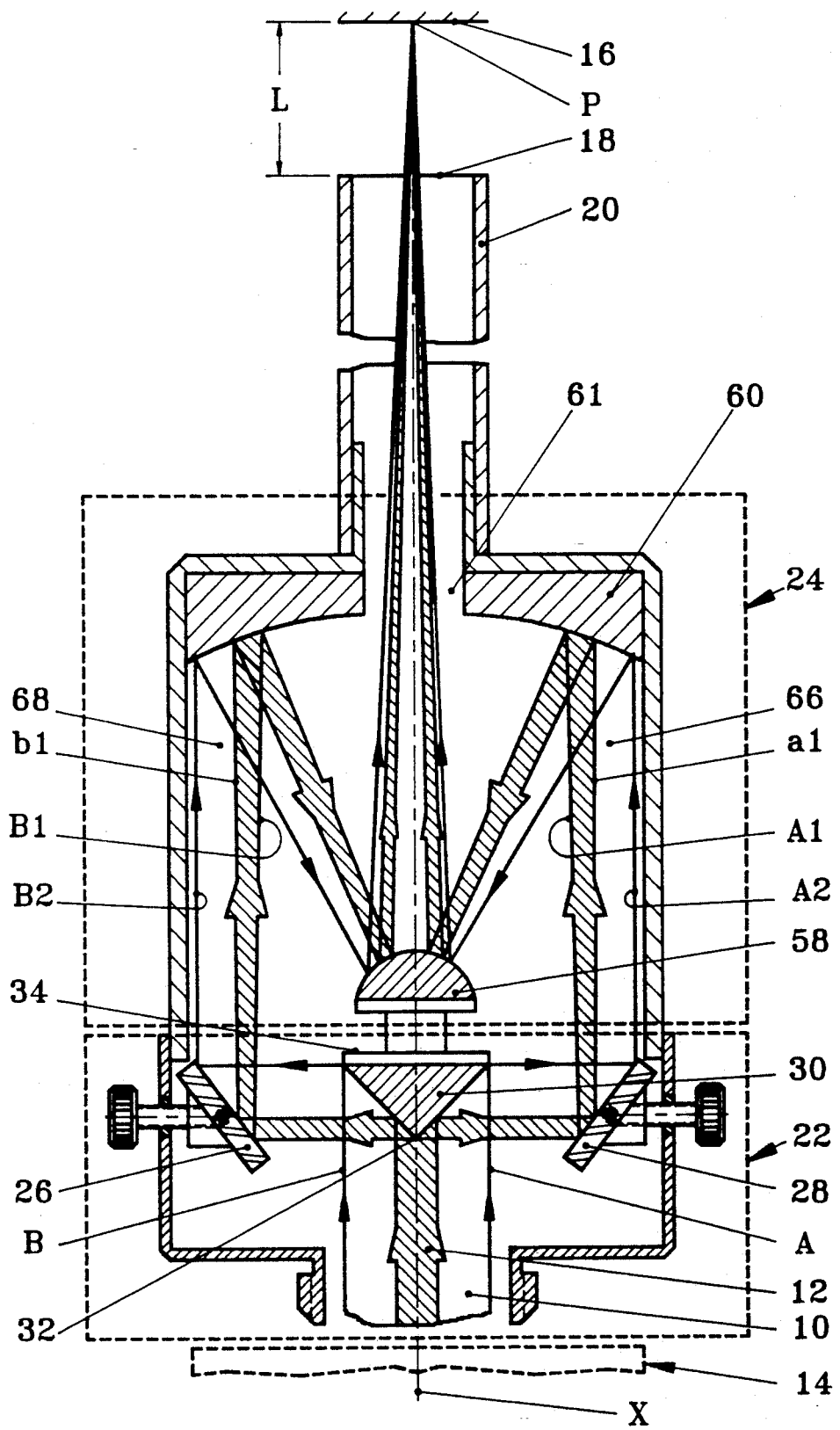
FIG. 1 is a schematic view of an endoscopic laser beam delivery system of the invention with a beam splitting module.

10—surgical laser beam
12—visible aiming beam
14—laser source
16—operation site
18—output end of the endoscopic tube
20—endoscopic tube
22—beam splitting module
24—mirror focusing unit
26, 28—plane mirrors
30—mirror prism
32—prism apex
38—axis
40—axle
42—rotating knob
44—block
46—vertical guide
48—screw
50—unthreaded end
52—threaded portion
54—threaded hole
56—stationary part
58—convex mirror
60—concave mirror
61—hole
62—aiming beam spot
64—surgical beam spot
66, 68—beam branches
70, 72—points of incidence of beams on the convex mirror
A1, A2, B1, B2,—boundary lines of the power-beam branches
A1, a1 and B1, b1—boundary lines of the aiming-beam branches
X—optical axis
P—target point
PM—central point of the deviated beam
$\theta$—misalignment angle
Y—adjustment direction of the plane mirrors
L—distance from endoscopic tube to the target FIG. 1—Overall Aiming and Endoscopic System An endoscopic mirror laser beam delivery system of the invention with a beam splitting module is schematically shown in FIG. 1.

This embodiment relates to the most typical case of an endoscopic laser beam delivery system in which an invisible high-power surgical laser beam 10 is defined by arrow boundary lines A and B and a visible, low-power aiming beam 12 is shown by densely hatched paths. The beams are to be delivered from two laser sources 14 (shown schematically in block form because they are not part of the invention) to an operation site 16 which is located at a predetermined distance L from the output end 18 of an endoscopic tube 20. As shown, aiming beam 12 and surgical beam 10 propagate along a common optical axis X. Aiming beam 12 is always smaller in diameter than surgical beam 10 so that it is always within the boundaries of lines A and B.

More specifically, the system consists of three major parts which will be considered separately, i.e., a laser beam splitting module 22, a two-mirror focusing unit 24, and endoscopic tube 20, the inlet end of which is connected to unit 24.

Laser beam splitting module 22 consists of a pair of plane mirrors 26 and 28. Mirrors 26 and 28 are inclined with respect to optical axis X at an angle of 45 and are symmetrical with respect to that axis.

An isosceles triangular mirror prism 30 with a right apex angle 32 is located symmetrically between mirrors 26 and 28 so that its apex is arranged on optical axis X and faces incident laser beams 10 and 12.

Splitting module 22 splits each laser beam into two components arranged symmetrically with respect to axis X. One split component is defined by boundary lines A1 and A2, while the other is defined by boundary lines B1 and B2.

In the illustrated embodiment, the width 34 of prism 30 is equal to the diameter of surgical beam 10.

Figure 2:
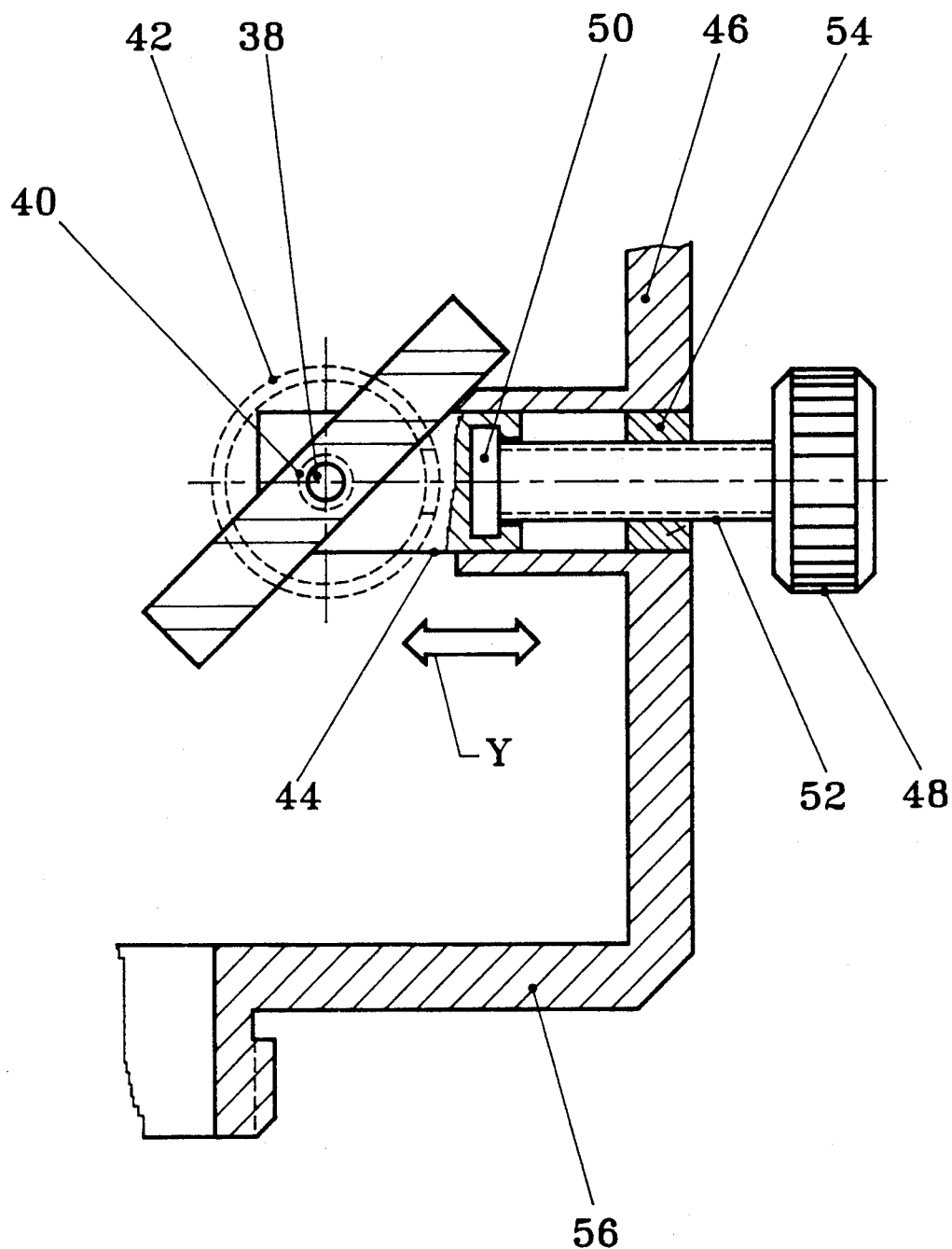
FIG. 2 is an example of a mechanism for adjusting positions of the mirror.

FIG. 2—Mirror Adjuster

Each of mirrors 26 and 28 is supported by a respective adjustment mechanism. Since both mechanisms are identical, only one of them, i.e., for mirror 26, will be described and is shown in FIG. 2.

The purpose of the adjustment mechanism is to ensure two independent adjustments in the position of the mirror. I.e., each mirror, which can be rotated in the plane of FIG. 1 around axis 38 (for mirror 26), is also displaceable in a direction Y, which is perpendicular to optical axis X and which also is in the plane of FIG. 1.

Mirror 26 is rigidly attached to an axle 40 which in turn is connected to a knob 42. The angular position of mirror 26 can be adjusted by manually rotating knob 42.

Axle 40 is supported by a block 44 which slides in a vertical guide 46 and is driven by a screw 48. An unthreaded end 50 of screw 48 is rotatingly installed into block 44, but is fixed against axial movements. A threaded portion 52 of screw 48 is screwed into a threaded hole 54 formed in a stationary part 56. As a result, rotation of screw 48 will displace block 44 together with mirror 26 in vertical direction Y.

The above mechanism has been shown as an example. Mirrors 26 and 28 can be adjusted by many other mechanisms, provided they allow both adjustments.

FIG. 1—Two-Mirror Focusing Unit

A second major device of the system is two-mirror focusing unit 24. One side of focusing unit 24 is connected to splitting module 22, while its other side is connected to operating channel or endoscopic tube 20. The units can be connected permanently or removably by any suitable means.

Focusing unit 24 comprises a convex mirror 58 which is located closer to prism 30 than a concave mirror 60. Mirror 58 has a flat side facing base 34 of mirror prism 30. Concave mirror 60 is located on the endoscopic side of focusing unit 24; mirror 60 has a central hole 61 for passing the beam focused by unit 24 into endoscopic tube 20.

The focusing system is arranged so that the reflecting surfaces of mirrors 58 and 60 face each other.

Endoscopic tube 20 guides laser beams received from focusing unit 24 and delivers these beams to operation site 16. Mirror 58 has curvature designated to guide aiming beam 12 and surgical beam 10 through the interior of tube 20 without interfering with the inner walls of tube 20.

Beam splitting unit 22 and focusing system 24 are designed so that both laser beam spots on the surface of operation site 16 will have the same diameter and will coincide. This will be described in detail later with reference to FIGS. 3 and 4.

FIGS. 1 to 4—Operation

The endoscopic laser beam delivery system is assembled as shown in FIG. 1 and consists of lasers 14, beam splitting unit 22, and focusing unit 24. Both plane mirrors 26 and 28 are adjusted so that the angles between their respective planes and optical axis X are equal to each other and to 45°. In addition, the plane of each mirror must be equally spaced from respective side surfaces of mirror prism 30. Such an adjustment is achieved by means of mechanism 36 shown in FIG. 2 by rotating respective knobs 42 and screws 48 until both mirrors assume the required positions, with both visible beam spots coinciding in one target point on tissue 16.

The spots are observed exactly in the same manner as will be described below with regard to the field of vision of the surgeon, as shown in FIGS. 4 and 5.

Operation of the endoscopic laser beam delivery system will be described with reference to the case of delivery surgical beam 10 and aiming beam 12 to a predetermined point P of tissue 16. As has been mentioned above, the spots of both beams must be aligned and have the same diameter. In other words, under normal conditions, which are shown in FIG. 3, aiming beam spot 62 must coincide with surgical beam spot 64.

Prior to operation, a surgeon at first switches on visible low-power aiming beam 12 and aims it onto target point P (FIG. 1). This beam falls along optical axis X onto mirror prism 30 which splits it symmetrically into two branches which are shown by densely hatched paths (FIG. 1). One of these branches is defined by boundary lines A1 and a1, and the other by boundary lines B1 and b1. Both branches of beam 12 are directed to inclined plane mirrors 26 and 28. Upon reflection from mirrors 26 and 28, the beam branches are guided in the form of parallel paths onto peripheral portions of concave mirror 60 (FIG. 1). Concave mirror 60 directs both beams onto convex mirror 58. The latter guides both beams independently in a converging form through endoscopic tube 20 to tissue 16 where the positions and dimensions of the beams coincide.

When the surgeon observes the operation site in the system with both visible aiming beams being properly aligned, he/she sees only one aiming beam spot. This spot is composed of spots 62 and 64 which correspond to visible portions of both branches 66 and 68. In other words, when the optical system is aligned, the surgeon sees a single spot with the center in point P, i.e., the surgeon sees a picture of the type shown in FIG. 3. All the operations described above relate only to the visible or low-power aiming beam; the invisible or high-power beam has not been activated yet.

Assume that the optical laser beam delivery system has misalignment, e.g., convex mirror 58 is slightly inclined, for example by angle $\theta$ (FIG. 4) with respect to its optical axis X. In this case, the visible beams will follow the paths shown by densely hatched paths in FIG. 4 which is a schematic optical diagram illustrating deviation of the beams in a misaligned system.

It can be seen that branches of the visible beam do not fall onto mirror 58 symmetrically, whereby reflections of these branches will not be projected onto the same target point P. Specifically, the surgeon will see a picture of the type shown in FIG. 5 which illustrates different positions of spots produced by both branches.

In other words, on tissue 16 the surgeon will see the branch defined between boundary lines A1 and a1 in target point P to which he/she aimed both branches, while another branch, i.e., the one defined between boundary lines B1and b1 will experience a lateral shift and will be seen on tissue 16 in the form of a second visible spot 64 (FIGS. 3 and 5) with a central point PM.

In the case of misaligment caused by displacement of convex mirror 58, the surgeon does not activate the power laser source (in block 14) and does not initiate operation until the misalignment is eliminated.

If both branches of the visible beam coincide in one point P, the system is properly aligned, and the surgeon initiates the power beam which is broader than the aiming or visible beam so that it always overlaps the latter. In FIG. 1, the power beam emitted from laser source 14 is limited by boundary lines A and B. The power beam passes through the same optical paths as the aiming beam, i.e., it falls along optical axis X onto mirror prism 30 which splits it symmetrically onto two branches 66 (which is limited between boundary lines A1 and A2) and 68 (which is limited between boundary lines B1 and B2, FIG. 1). Both branches 66 and 68 are directed to inclined plane mirrors 26 and 28. Upon reflection from mirrors 26 and 28, the power beam branches are guided in the form of parallel paths onto peripheral portions of concave mirror 60 (FIG. 1). Concave mirror 60 directs both beams onto convex mirror 58. The latter guides both beams independently in a converging form through endoscopic tube 20 to tissue 16 where the positions and dimensions of the beams coincide. The surgeon can be confident that both power beam branches will coincide because they follow the same paths which have been visually controlled by checking positions of the aligned visible beam branches, as has been described earlier.

Elimination of misalignment is beyond the scope of the present invention, which is aimed only at a reliable means for detecting misalignments. Moreover, the misaligment can be caused by manufacturing defects which can be eliminated only by replacing entire mirror 58, or the mirror can be slightly tilted during transportation. In any case, the system may incorporate any conventional mechanism adjusting the angular position of convex mirror 58, e.g., by installing this mirror on an adjustable spherical universal joint (not shown). Furthermore, slight misalignment (when $\theta$ is about 1°) can be eliminated by changing positions of plane mirror 26 and 28 with the help of adjustment mechanisms 36. For example, in the case of FIG. 4, asymmetry in the position of points 70 and 72 of incidence of laser beams onto the surface of convex mirror 58 can be corrected by turning and shifting mirror 26 with respect to mirror 28.

Summary, Ramifications, Scope

Thus, our endoscopic laser beam delivery system includes a beam splitting module which ensures visual control of alignment and focusing of two coaxial beams. The system eliminates central obscuration of laser beams delivered to an operation site. It ensures small spot sizes, improves alignment of beams, reduces transmission losses, and can operate in areas remote from the outlet end of the endoscopic tube. In addition, a new and reliable method is provided for visually controlling alignment and focusing of both aiming and power beams onto a selected target point.

In other words, the endoscopic laser beam delivery system is designed in such a manner that, by using a beam splitting device, it eliminates central obscuration of the thin aiming beam, which otherwise would not pass through the system at all. At the same time it allows alignment to be visually inspected. As a result, a surgeon, who observes positions of laser beam spots, is always confident that the system is properly aligned.

Although the endoscopic laser beam delivery system has been shown and described in the form of one specific embodiment, this embodiment, its parts, materials, and configurations have been given only as examples, and many other modifications of system are possible. For example, endoscopic tube 20 may have two parallel channels, one for delivering the laser beams, and another for viewing the operation site. Mechanism 36 for adjusting positions of mirror 26 and 28 can be embodied in many other forms, e.g., the mirror can be installed on universal joints with displaceable axes. The power beam can be visible, as well as invisible, and can either be pulsed or continuous.

Therefore, the scope of the invention should be determined, not by the example given, but by the appended claims an their legal equivalents.

What we claim is:

1. An endoscopic mirror laser bean delivery system comprising:
    a beam splitting module for optical connection to a laser beam source which supplies at least one incident laser beam to said module along an optical axis of said module, said module dividing said laser beam into two symmetrical branches;
    a two-mirror focusing unit optically connected to said beam splitting unit to receive said two branches and to direct them onto a common target point;
    an endoscopic tube for building said two focused branches onto said common target point without obstruction, said tube having a rear end which is connected to said focusing unit and a front end which faces said common target point, said common target point being spaced from said front end;
    said beam splitting module comprising a mirror prism having an apex facing said incident laser beam and located on said optical axis, and a pair of plane mirrors arranged symmetrically on both sides of said central axis and inclined at equal angles to said axis, so that when said incident laser beam falls onto said prism, it is divided into said two symmetrical branches;
    an aspherical concave mirror having a curved portion facing said beam splitting module; and
    a central convex mirror having a curved portion facing said curved portion of said a spherical concave mirror and said target point, so that when said two branches fall onto said a spherical concave mirror, said two branches are directed in a converged form onto said convex mirror and are guided into said endoscopic tube through said hole without being obstructed by said convex mirror.

2. The endoscopic mirror laser beam delivery system of claim 1, further including means for adjusting the positions of said plane mirrors with respect to said axis.

3. The endoscopic mirror laser beam delivery system of claim 2 wherein said means for adjusting is arranged to displace said plane mirror in a direction perpendicular to said axis and rotate said mirror around a plurality of horizontal axes.

4. An endoscopic mirror laser beam delivery system comprising:
    a beam splitting module for optical connection to a laser beam source which supplies at least one incident laser beam to said module along an optical axis of said module, said module dividing said laser beam into two symmetrical branches;
    a two-mirror focusing unit optically connected to said beam splitting module to receive said two branches and to direct them onto a common target point;
    an endoscopic tube for guiding said two focused branches onto said common target point without obstruction, said tube having a rear end which is connected to said focusing unit and a front end which faces said common target point, said common target point being spaced from said front end;
    said beam splitting module comprising a mirror prism having an apex facing said incident laser beam and located on said optical axis, and a pair of plane mirrors arranged symmetrically on both sides of said central axis and inclined at equal angles to said axis, so that when said incident laser beam falls onto said prism, it is divided into said two symmetrical branches;

an aspherical concave mirror having a curved portion facing said beam splitting module;

a central convex mirror having a curved portion facing said curved portion of said a spherical concave mirror and said target point, so that when said two branches fall onto said a spherical concave mirror, said two branches are directed in a converged form onto said convex mirror and are guided into said endoscopic tube through said hole without being obstructed by said convex mirrors; and means for adjusting the positions of said plane mirrors with respect to said axis.

5. The endoscopic mirror laser beam delivery system of claim 4 wherein said means for adjusting is arranged to displace said plane mirror in a direction perpendicular to said axis and rotate said mirror around a plurality of horizontal axes.

* * * * *

UNITED STATES PATENT AND TRADEMARK OFFICE
CERTIFICATE OF CORRECTION

PATENT NO. : 5,163,936
DATED : Nov 17, 1992
INVENTOR(S) : M. Black and V. Kuperschmidt It is certified that error appears in the above-indentified patent and that said Letters Patent is hereby corrected as shown below:

Col. 8, lines 35 and 37, change "a spherical" to —aspherical—.
Col. 9, line 11, and col. 10, line 1, change "a spherical" to —aspherical—.

Signed and Sealed this

Tenth Day of May, 1994

Attest:

BRUCE LEHMAN

*Attesting Officer*   *Commissioner of Patents and Trademarks*